(12) United States Patent
Guala

(10) Patent No.: US 7,624,749 B2
(45) Date of Patent: Dec. 1, 2009

(54) FLOW REGULATOR FOR MEDICAL LIQUIDS AND METHOD FOR ITS FABRICATION

(75) Inventor: Gianni Guala, Turin (IT)

(73) Assignee: Industrie Borla S.p.A., Moncaleri (Turin) (IT)

(*) Notice: Subject to any disclaimer, the term of this patent is extended or adjusted under 35 U.S.C. 154(b) by 715 days.

(21) Appl. No.: 11/450,707

(22) Filed: Jun. 9, 2006

(65) Prior Publication Data

US 2007/0018129 A1 Jan. 25, 2007

(30) Foreign Application Priority Data

Jun. 9, 2005 (IT) .......................... TO2005A0394

(51) Int. Cl.
*F16K 3/00* (2006.01)
(52) U.S. Cl. .................... 137/15.18; 137/553; 137/556; 137/556.6; 251/208; 251/205; 604/248; 116/277
(58) Field of Classification Search ................ 137/553, 137/556, 556.3, 556.6, 501, 15.17, 15.18, 137/315.17; 251/205, 208, 340, 341, 209; 604/248, 32, 246; 116/277
See application file for complete search history.

(56) References Cited

U.S. PATENT DOCUMENTS

| | | | | |
|---|---|---|---|---|
| 3,253,612 A | * | 5/1966 | Curatola et al. ............. | 137/553 |
| 3,913,607 A | * | 10/1975 | Price, John H. .......... | 137/556.6 |
| 4,577,831 A | * | 3/1986 | DiBartolo .................... | 251/205 |
| 4,917,687 A | * | 4/1990 | O'Boyle ...................... | 604/248 |
| 5,234,413 A | | 8/1993 | Wonder et al. .............. | 604/248 |
| 6,213,149 B1 | * | 4/2001 | Moner ...................... | 137/556.3 |
| 7,028,927 B2 | * | 4/2006 | Mermet ...................... | 137/556 |

FOREIGN PATENT DOCUMENTS

| | | |
|---|---|---|
| EP | 1 312 388 A1 | 5/2003 |
| EP | 1 312 388 B1 | 12/2004 |

OTHER PUBLICATIONS

European search report for EP 06115185.8—2310, dated Aug. 30, 2006.

* cited by examiner

*Primary Examiner*—Stephen Hepperle
*Assistant Examiner*—Andrew J Rost
(74) *Attorney, Agent, or Firm*—Heslin Rothenberg Farley & Mesiti P.C.; Victor A. Cardona, Esq.

(57) ABSTRACT

A flow regulator for medical liquids comprising a first body and a second body coupled to one another in a rotatable way and a gasket set between them and overmolded on the second body. Provided thereon is at least one graduated scale formed by impressions and/or, respectively, by reliefs integral with the second body, and by inserts and/or, respectively, by complementary openings of a side skirt of the overmolded gasket.

10 Claims, 4 Drawing Sheets

FLOW REGULATOR FOR MEDICAL LIQUIDS AND METHOD FOR ITS FABRICATION

CROSS-REFERENCE TO RELATED APPLICATIONS

This application claims priority from Italian Patent Application No. TO2005A000394, filed Jun. 9, 2005, the entire disclosure of which is incorporated herein by reference.

FIELD OF THE INVENTION

The present invention relates in general to the administration of medical liquids, and regards more in particular a flow regulator for precision dosage of said liquids.

BACKGROUND OF THE INVENTION

Known from document EP-B-1312388 is a precision flow regulator comprising a first body having a tubular inlet connector and a second body having a tubular outlet connector.

The first and second bodies are made of moulded plastic material and are coupled to one another in such a way that they can rotate with respect to one another about an axis of rotation, with the interposition of a gasket made of elastomeric material. At least one dosing passage is provided between the first and second bodies and through said gasket to open the communication between said inlet connector and said outlet connector progressively by means of the relative rotation between said first and second bodies. In the flow regulator according to the already cited document EP-B-1312388, the first body has a wall facing the second body, formed with a plurality of dosing grooves, which have differentiated sections and lengths, set concentrically with respect to the axis of rotation and selectable, via the relative rotation between the first and second bodies, to set the inlet connector in communication with the outlet connector through a hole in the gasket made of elastomeric material.

A similar flow regulator, equipped, however, with a single dosing groove with variable cross section, is also described in document U.S. Pat. No. 5,234,413.

For the production of the above flow regulators three distinct operations are required for moulding, normally injection moulding, of the three components (first body, second body and gasket), and then a further operation of assembly. Furthermore, said flow regulators are necessarily equipped with at least one graduated scale, and more typically two graduated scales arranged peripherally along the side wall of the second body, as well as with a pointer associated to the first body and co-operating with the graduated scale or each graduated scale for visualizing the relative angular position between the first and second bodies, corresponding to the selectively set regulation of the flow of liquid from the inlet connector to the outlet connector through the aforesaid at least one dosing passage. The graduated scale or scales and the pointer (not illustrated in the aforesaid prior documents but necessarily present on the flow regulators built according to said documents, as available on the market) require further operations of printing (normally silk-screen printing) to be carried out, respectively, on the first body and on the second body prior to their mutual assembly.

SUMMARY OF THE INVENTION

The purpose of the present invention is to simplify the fabrication of the flow regulator defined above so as to reduce appreciably the costs of production thereof.

According to the invention said purpose is achieved thanks to the fact that the aforesaid at least one graduated scale includes impressions and/or, respectively, reliefs formed integrally by moulding on said second body, and to the fact that the gasket consists of an element overmoulded on said second body and has a side skirt formed with openings and/or inserts coupled in a complementary way, respectively, to said reliefs and/or to said impressions of said second body to complete said at least one graduated scale.

Thanks to the above idea of solution the fabrication of the flow regulator according to the invention can be obtained using simplified equipment as regards moulding of its components, and moreover eliminates the need to provide printing equipment for the graduated scale or each graduated scale. In fact, moulding of the second body and of the gasket overmoulded thereon can be obtained in a single mould, with the simultaneous formation of the graduated scale or each graduated scale using the material of the gasket, which fills the impressions or, respectively, surrounds the reliefs previously formed integrally on the second body.

According to another advantageous characteristic of the invention, the pointer consists of an integral side appendage of the first body, conveniently shaped like a window. This also enables elimination of the supplementary operation of forming of the pointer by printing subsequent to moulding of the first body.

According to a preferred embodiment of the invention, the flow regulator is equipped with two graduated scales, formed one by impressions and the other by reliefs of the second body, as well as by corresponding inserts and openings of the gasket made in the process of its overmoulding on the second body.

The graduated scales can moreover be integrated with wordings indicating the condition of opening or closing of the flow regulator, obtained with the same modalities, and moreover the side skirt of the overmoulded gasket can also conveniently form on the second body a perimetral gripping edge, designed to facilitate manipulation and regulation also with a just one hand.

Also forming the subject of the invention is a method for the fabrication of the flow regulator defined above, basically characterized in that it comprises the following steps:

moulding said first body within a first mould and said second body within a second mould with said integral impressions and/or reliefs;

overmoulding said gasket on said second body within said second mould so that said elastomeric material will fill and/or surround said impressions and/or, respectively, said reliefs; and fitting said first and second bodies to one another in a mutually rotatable way.

BRIEF DESCRIPTION OF THE DRAWINGS

The invention will now be described in detail with reference to the annexed plate of drawings, which is provided purely by of way of non-limiting example and in which.

DETAILED DESCRIPTION OF THE INVENTION

Figure 1:
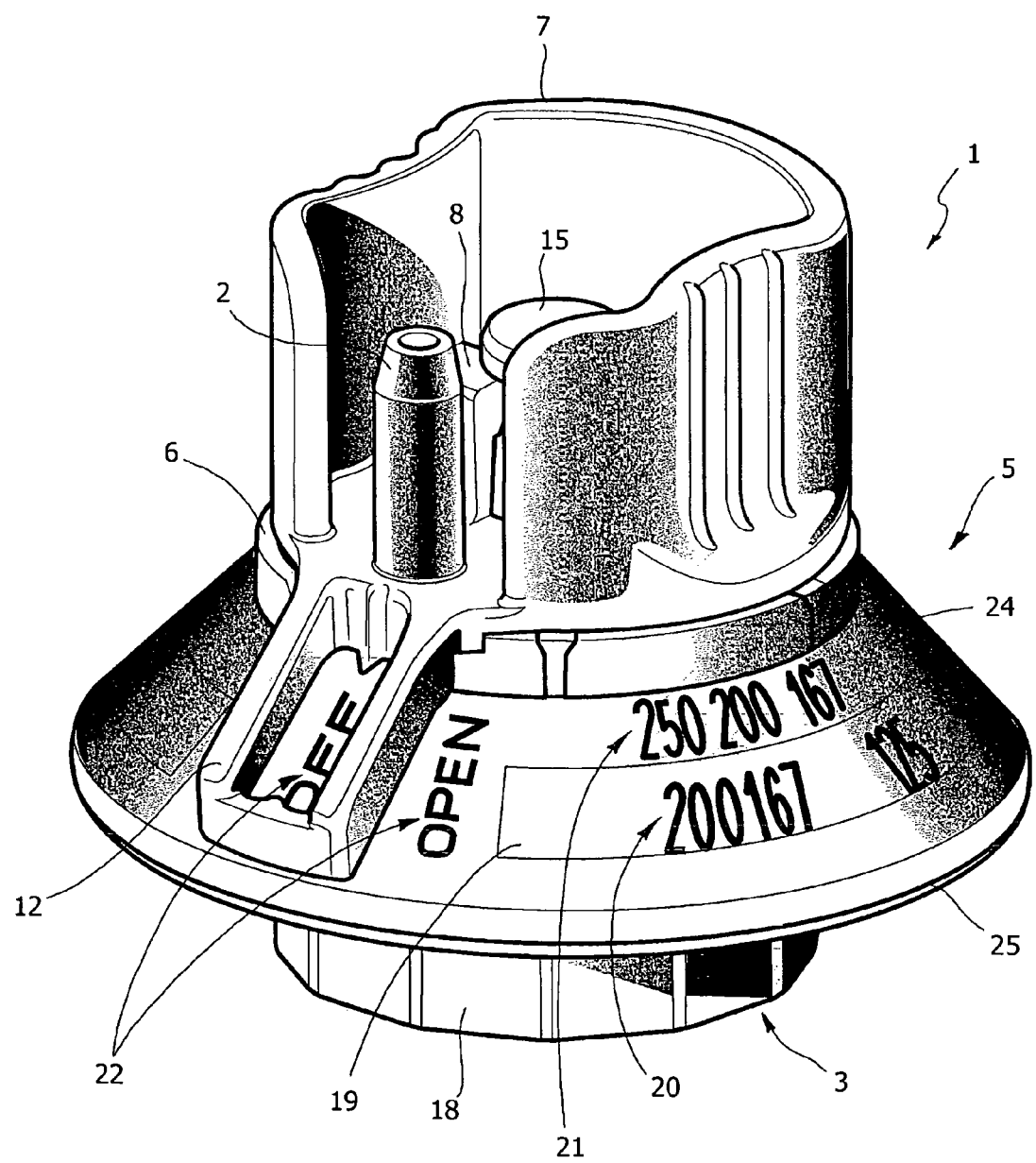
FIG. 1 is a schematic perspective view of a flow regulator for medical liquids according to the invention.
Figure 2:
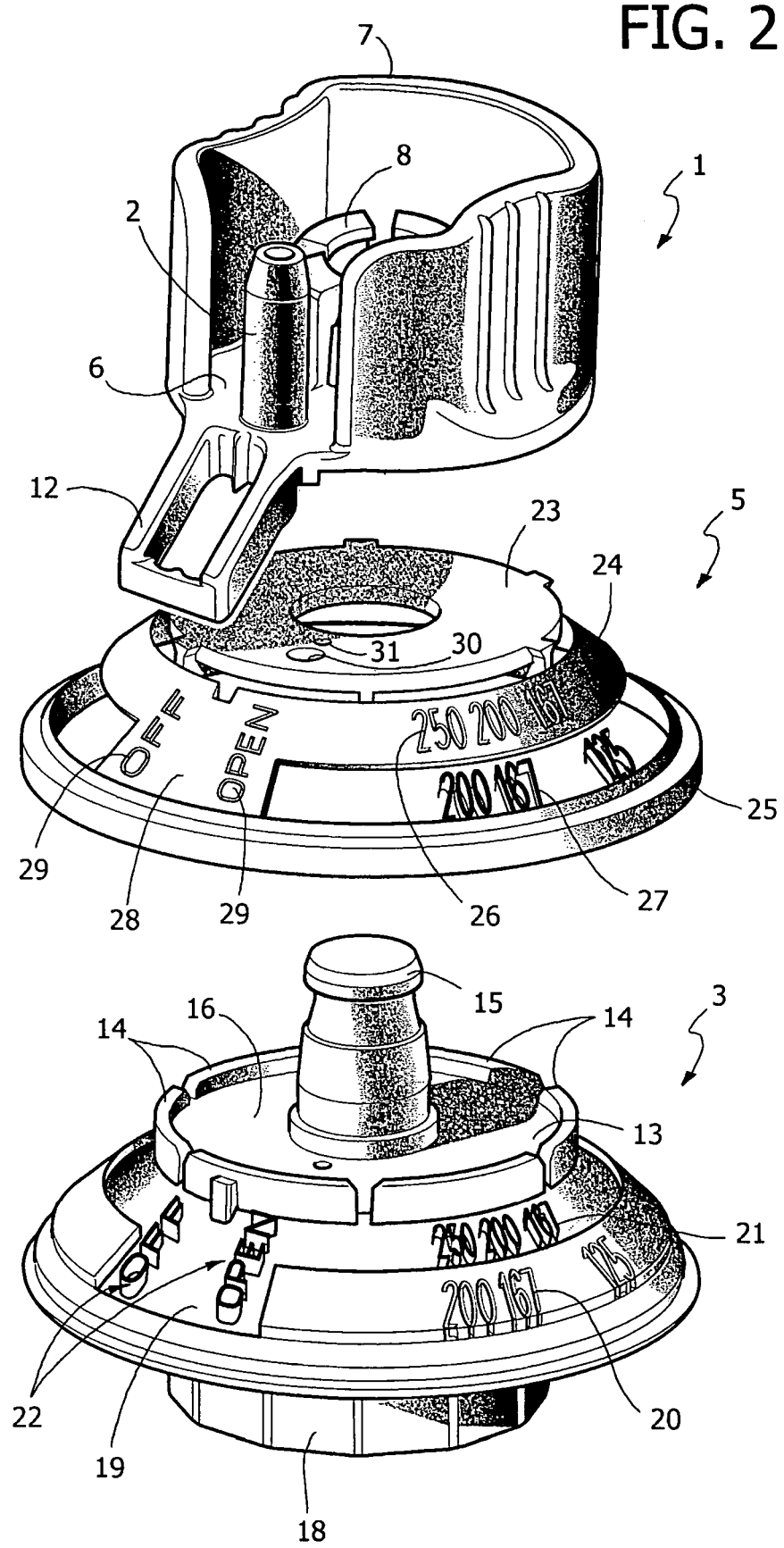
FIG. 2 is an exploded view of the flow regulator of FIG. 1.

With reference to the drawings, a flow regulator for medical liquids according to the invention comprises in a way generally in itself known (for example, from already cited document EP-B-1 312 388) a first body 1 having a tubular inlet connector 2, a second body 3 having a tubular outlet connector 4, and a gasket made of elastomeric material or thermoplastic elastomer 5, set between the first body 1 and the second body 3. It should be noted that, for the reasons clarified in what follows, the representation of the gasket 5 in FIG. 2 is fictitious, in so far as according to the invention said gasket 5 does not exist as a unit in itself, but is instead integrated with the second body 3.

The first body 1, formed by injection moulding of a plastic material, comprises in a single piece a plane base wall 6, from which there project axially: the tubular inlet connector 2; a side skirt 7 shaped ergonomically and open in a position corresponding to the tubular connector 2, and a central boss 8 formed by elements that can divaricate elastically.

Figure 3:
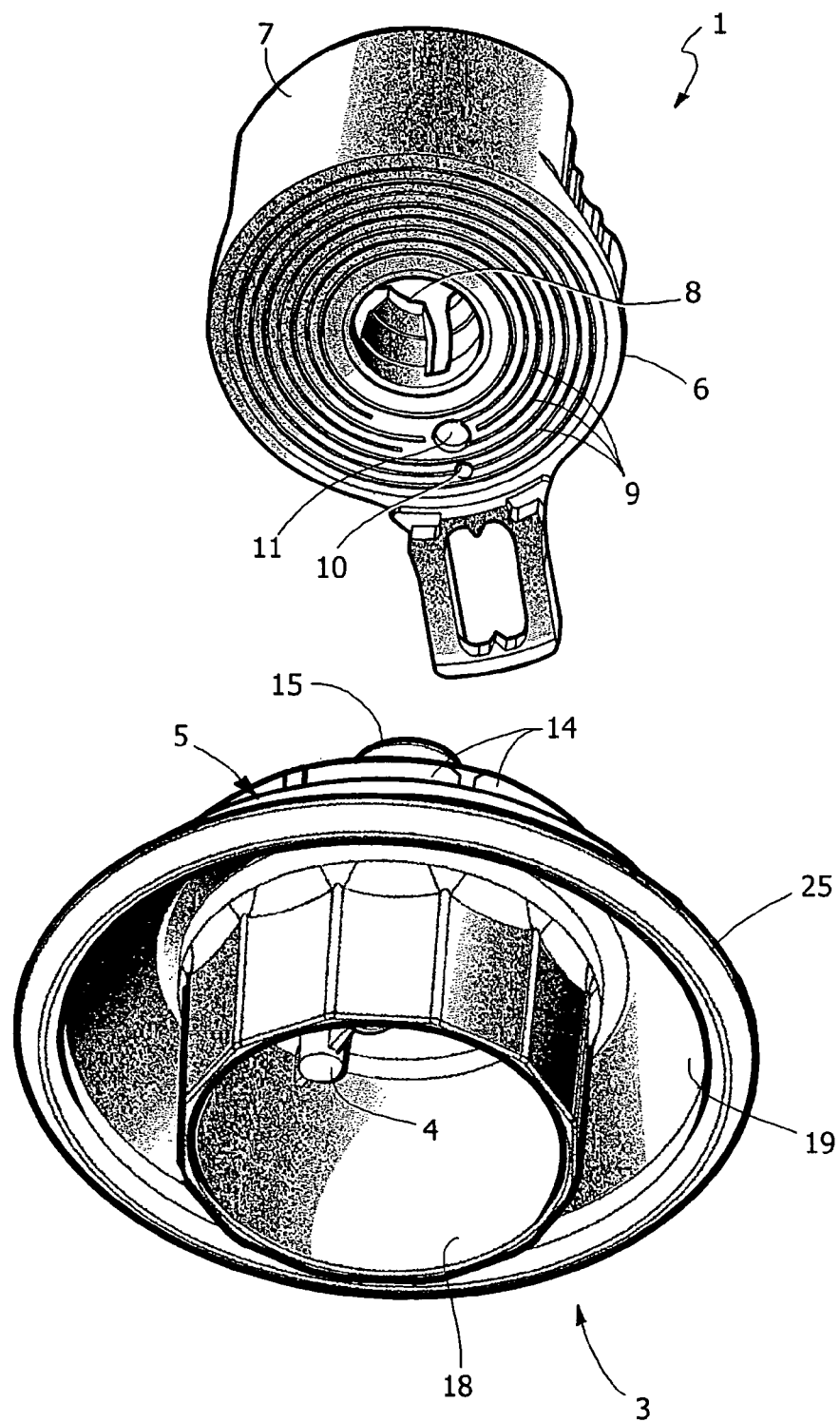
FIG. 3 is a partially exploded view from beneath of the flow regulator of FIG. 1.
Figure 4:
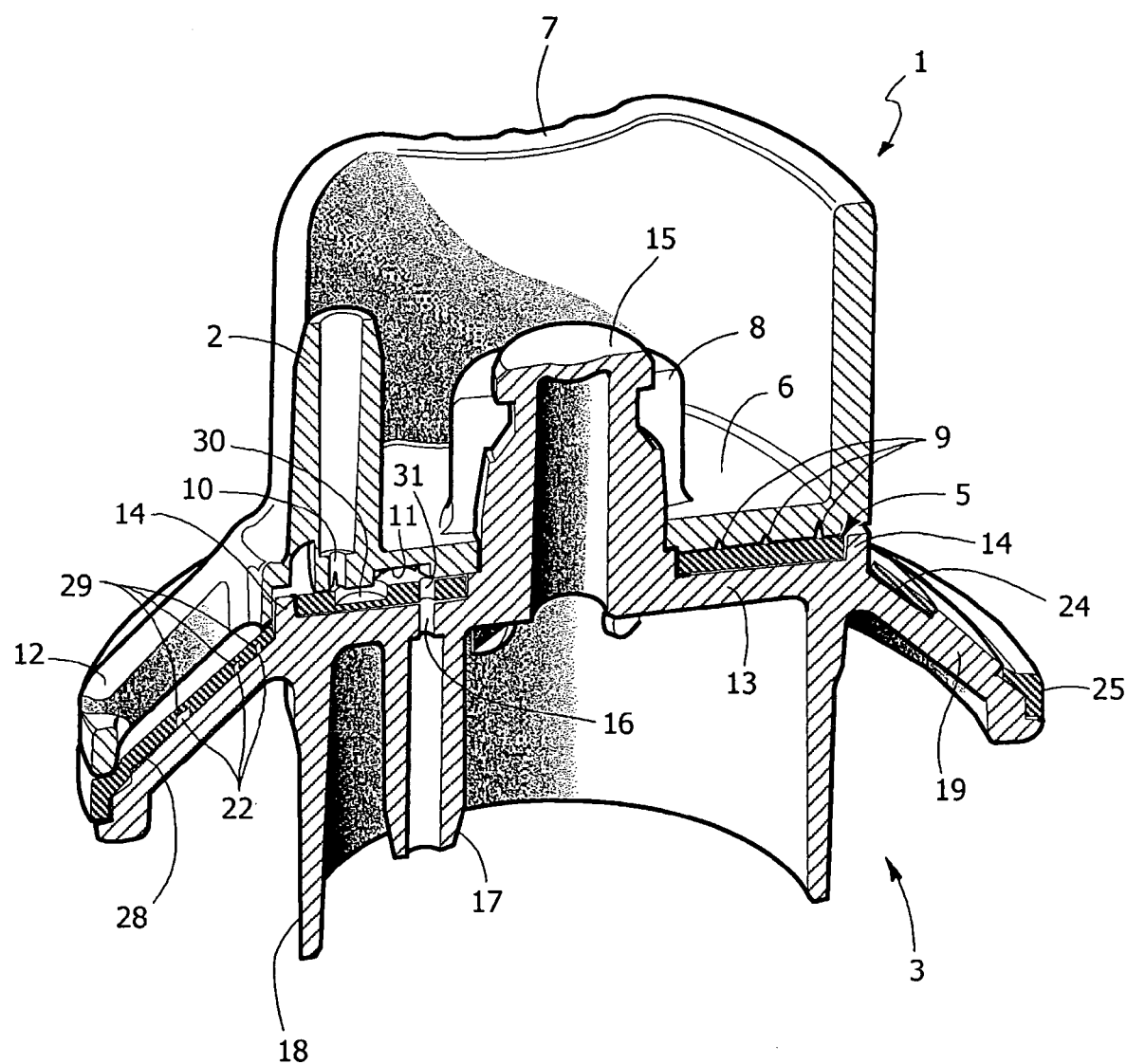
FIG. 4 is a view in axial cross section of the flow regulator.

As is illustrated in detail in FIG. 3, the base wall 6 is formed, in a position corresponding to the face thereof set facing the second body 3, with a series of dosing grooves 9, which are set concentrically to the boss 8 and have different lengths and/or sections. Furthermore, the wall 6 has a through hole 10 in communication with the inlet connector 2 and a recess 11 that opens towards the grooves 9.

According to the invention, the first body 1 is moreover formed integrally with a projecting side appendage shaped like a window 12, which, as will be seen in what follows, defines a pointer.

The second body 3, which is also made of moulded plastic material, has a top wall 13, delimited peripherally by axial sectors 14 and from which there projects centrally an integral pin 15 shaped so as to engage by snap action in a rotatable way within the boss 8 of the first body 1.

The top wall 13 has a through hole 16 in communication with a tubular outlet connector 17 radially staggered with respect to the tubular inlet connector 2 of the first body 1 and projecting within a circumferential skirt 18 formed integrally with the body 3.

Between the wall 13 and the skirt 18 the second body 2 is moreover formed integrally with a circumferential side flange 19, partially formed on which are a first graduated scale and a second graduated scale designated as a whole by 20 and 21, which indicate (with different units of measurement) the flow of liquid that, in use, traverses the regulator, entering the inlet connector 2 and exiting through the outlet connector 17.

The first graduated scale 20 is in low relief, i.e., the numbers that represent it are formed by figures impressed in the perimetral flange 19, whilst the second graduated scale 21 is in high relief, i.e., the numbers that make it up are formed by figures projecting from the perimetral flange 19. It should be noted that the configuration could be reversed, in the sense that the scale 20 could be in high relief and the scale 21 in low relief.

Also integrally formed on the side flange 19 are wordings 22 indicating the condition of complete closing and of initial opening of the regulator; also the wordings 22 are in high relief, being formed by letters projecting from the perimetral flange 19.

The gasket 5 includes a plane annular element 23, having dimensions corresponding to those of the top wall 13 of the second body 3 and of the base wall 6 of the first body 1. Integrally formed with said annular element 23 are a first ring 24 and a second ring 25 set on top of the perimetral flange 19 of the second body 3. The first ring 24 is formed with openings, which are designated as a whole by 26 and have a shape complementary to the numbers in high relief of the second graduated scale 21 of the body 3. The second ring 25 is formed integrally with inserts, which are designated as a whole by 27 and have shapes complementary to those of the numbers in low relief that make up the first graduated scale 20 of the second body 3. Said second ring 25 moreover coats the peripheral edge of the perimetral flange 19 of the second body 3, defining a peripheral manual-gripping part.

The rings 24 and 25 are interconnected by a bridge 28 formed with openings designated as a whole by 29, which have a shape complementary to the wordings in high relief 22 of the second body 3.

The annular element 23 is moreover formed with a recess 30 facing the base wall 6 of the first body 1 and with a through hole 31 in communication with the tubular outlet connector 17 of the second body 3.

As clarified previously, the gasket 5 as a whole does not constitute an element in itself (as is instead fictitiously represented in FIG. 2), given that it is—according to the invention—integrated with the second body 3.

The method of fabrication of the flow regulator according to the invention envisages the steps described hereinafter.

The first body 1 and the second body 3 are formed by injection moulding of a suitable plastic material, respectively, within a first mould and within a second mould. Following upon moulding of the second body 3, injected within the corresponding second mould is the thermoplastic elastomer that is to constitute the gasket 5 as a whole (annular element 23 and rings 24 and 25), which in this way is directly overmoulded on the second body 3. The second mould will be shaped so that, following upon the overmoulding of the gasket 5, the material corresponding to the first ring 24 and to the bridge 28 surrounds the numbers in high relief of the second graduated scale 21 and the wordings in high relief 22, and the material that constitutes the second ring 25 fills the numbers in low relief corresponding to the first graduated scale 20. In this way, the graduated scales 20 and 21 are thus completed directly within the second mould without any need to carry out further supplementary printing operations. In order to render the graduated scales 20 and 21 and the wordings 22 more immediately and clearly visible, the plastic material used for making the second body 3 and the thermoplastic rubber used for making the gasket 5 will conveniently present colourings that are different and in contrast with one another: for example, the first white, and the second blue.

Once the steps of moulding are thus completed, the first body 1 and the second body 3 with the gasket 5 overmoulded thereon are coupled to one another in a rotatable way, introducing and blocking the pin 15 within the boss 8 by snap action. Following upon assembly, the pointer constituted by the side appendage integral to the window 12 of the body 1 projects above said side skirt 24 of the gasket 5 and enables, in co-operation with one or other of the graduated scales 20 and 21, or else with the wordings 22, immediate visualization of the relative angular position between the first body 1 and the second body 3 corresponding to the regulation of flow selectively set by the operator. The setting can be made in an extremely easy and convenient way, thanks to the presence of the perimetral edge 25, even just using one hand.

The operation of the flow regulator thus assembled will not be described in detail in so far as it is generally conventional and substantially corresponds to what is described in already cited document EP-B-1312388.

Of course, the details of construction and the embodiments may vary widely with respect to what is described and illustrated herein, without thereby departing from the scope of the present invention, as defined in the ensuing claims.

Thus, for example, the dosing grooves 9 for opening progressively communication between the inlet connector 2 and said outlet connector 17 may be replaced by a single groove with a progressively decreasing cross section, and in this case operation of the flow regulator will substantially correspond to what is described in document U.S. Pat. No. 5,234,413, also previously cited, or else by one or more passages differently provided and configured.

What is claimed is:

1. A flow regulator for medical liquids comprising a first body having a tubular inlet connector and a second body having a tubular outlet connector, said first and second bodies being made of moulded plastic material and being coupled to one another in a mutually rotatable way about an axis of rotation with the interposition of a gasket made of elastomeric material, at least one dosing passage being provided between said first and second bodies and through said gasket to open progressively the communication between said inlet connector and said outlet connector by means of the relative rotation of said first and second bodies; said second body having at least one graduated peripheral side scale and said first body having a pointer co-operating with said at least one graduated scale for visualizing the relative angular position between said first and second bodies corresponding to the regulation selectively set of the flow of liquid from said inlet connector to said outlet connector through said at least one dosing passage, wherein said at least one graduated scale includes at least one of impressions and reliefs formed integrally by moulding on said second body, and said gasket consists of an element overmoulded on said second body and having a side skirt formed with at least one of openings and inserts coupled in a complementary way with at least one of said reliefs and said impressions of said second body for completing said at least one graduated scale.

2. The flow regulator according to claim 1, wherein said pointer consists of an integral side appendage of said first body.

3. The flow regulator according to claim 2, wherein said appendage is shaped like a window projecting above said side skirt of said gasket.

4. The flow regulator according to claim 1 provided with two graduated scales, the first formed by impressions of said second body and by corresponding inserts of said side skirt of said gasket and the second formed by reliefs of said second body and by corresponding openings of said side skirt and of said gasket.

5. The flow regulator according to claim 4, wherein said second graduated scale further includes wordings formed by reliefs of said second body and by corresponding openings of said side skirt of said gasket.

6. The flow regulator according to claim 1, wherein said side skirt of said gasket defines a perimetral gripping edge of said second body.

7. The flow regulator according to claim 1, wherein said second body and said gasket have different colourings.

8. A method for fabrication of a flow regulator according to claim 1, comprising the following steps:
   moulding said first body within a first mould and said second body within a second mould with said integral impressions and reliefs;
   overmoulding said gasket on said second body within said second mould so that said elastomeric material at least one of fills and surrounds at least one of said impressions and said reliefs; and
   fitting to one another in a mutually rotatable way said first and second bodies.

9. The method according to claim 8, wherein said pointer is formed integrally with said first body in said first mould.

10. The method according to claim 8, wherein said second body and said gasket are made with different colourings.

* * * * *